(12) United States Patent
McAndrew et al.

(10) Patent No.: US 6,736,827 B1
(45) Date of Patent: May 18, 2004

(54) LOW PROFILE CATHETER

(75) Inventors: Eamonn Joseph McAndrew, Galway (IE); Paula Marie McDonnell, Galway (IE)

(73) Assignee: Medtronic AVE, Inc., Santa Rosa, CA (US)

(*) Notice: Subject to any disclaimer, the term of this patent is extended or adjusted under 35 U.S.C. 154(b) by 0 days.

(21) Appl. No.: 09/687,563

(22) Filed: Oct. 13, 2000

(51) Int. Cl.[7] .............................. A61B 17/00
(52) U.S. Cl. ................. 606/194; 606/195; 606/198; 604/96.01
(58) Field of Search .................. 604/10, 9, 246, 604/247, 905, 256, 249, 236, 237, 264, 96.01, 523; 600/585; 606/194, 195, 198

(56) References Cited

U.S. PATENT DOCUMENTS

| | | | |
|---|---|---|---|
| 4,998,917 A | * | 3/1991 | Gaiser et al. ............ 604/96.01 |
| 5,135,487 A | | 8/1992 | Morrill et al. |
| 5,279,560 A | * | 1/1994 | Morrill et al. ............... 606/194 |
| 5,279,561 A | | 1/1994 | Roucher et al. |
| 5,324,259 A | * | 6/1994 | Taylor et al. ............ 604/99.04 |
| 5,417,658 A | | 5/1995 | Loney et al. |
| 5,441,484 A | | 8/1995 | Atkinson et al. |
| 5,454,788 A | | 10/1995 | Walker et al. |
| 6,071,285 A | | 6/2000 | Lashinski et al. |
| 6,190,332 B1 | * | 2/2001 | Muni et al. .................. 600/585 |

* cited by examiner

Primary Examiner—Brian L. Casler
Assistant Examiner—Matthew DeSanto
(74) Attorney, Agent, or Firm—Catherine C. Maresh; James F. CriHenden

(57) ABSTRACT

A medical device for stenting within a patient's vascular system is a low profile fixed-wire balloon catheter. The balloon is not attached directly to the wire-like structure of the catheter, providing a degree of independent rotation therebetween.

3 Claims, 3 Drawing Sheets

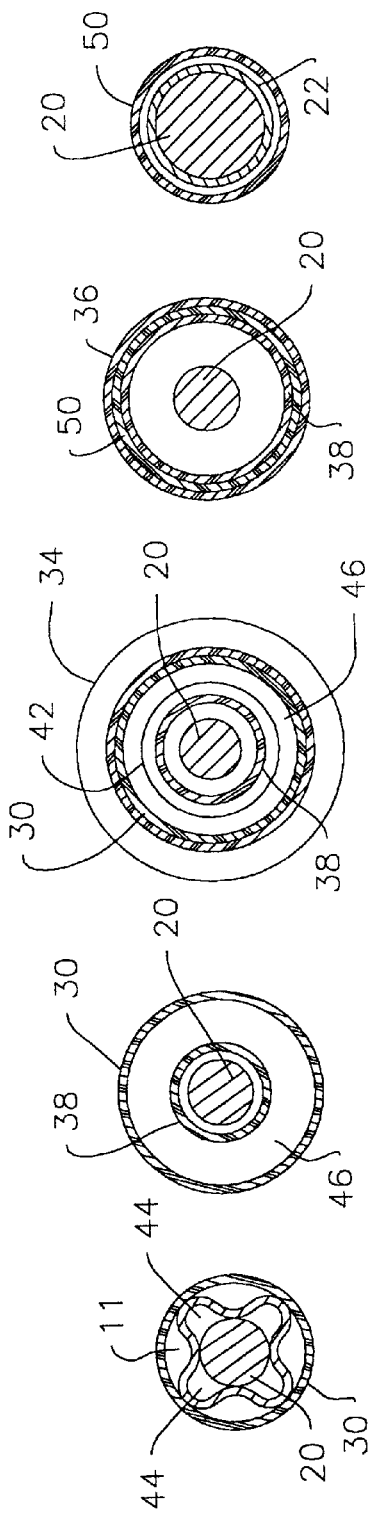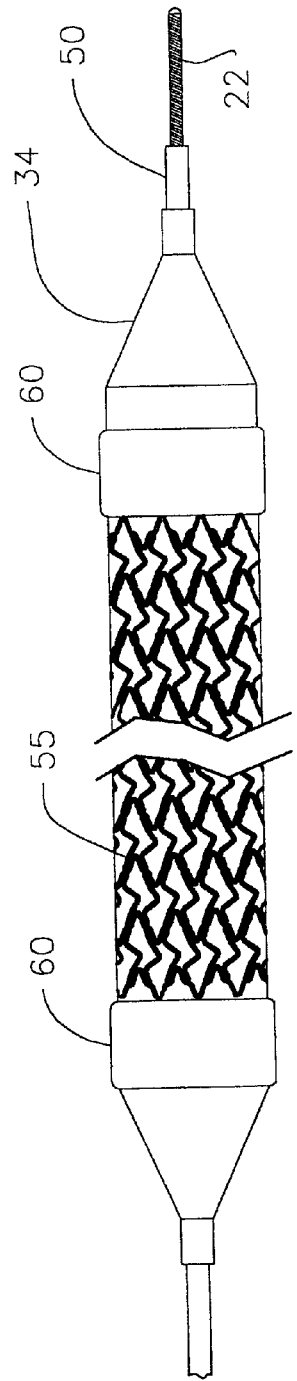

LOW PROFILE CATHETER

FIELD OF THE INVENTION

The invention relates to intraluminal endovascular stenting, and in particular, to a low profile fixed wire delivery catheter.

BACKGROUND OF THE INVENTION

Endovascular stenting is particularly useful for arteries which are blocked or narrowed and is an alternative to surgical procedures that intend to bypass the occlusion. The procedure involves inserting a prosthesis into a body tube and expanding it to prevent collapse of a vessel wall. While stenting has most commonly been used adjunctively, following an intervention such as angioplasty or atherectomy, there is increasing interest in primary, or direct stent placement.

Percutaneous transluminal angioplasty (PTCA) is used to open coronary arteries which have been occluded by a build-up of cholesterol fats or atherosclerotic plaque. Typically, a guide catheter is inserted into a major artery in the groin and is passed to the heart, providing a conduit to the ostia of the coronary arteries from outside the body. A balloon catheter and guidewire are advanced through the guiding catheter and steered through the coronary vasculature to the site of therapy. The balloon at the distal end of the catheter is inflated, causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

A stent is typically a cylindrically shaped device formed from wire(s) or a tube and is intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during an angioplasty procedure by using a balloon catheter bearing a compressed stent which has been loaded onto the balloon. The stent radially expands as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

A balloon of appropriate size and pressure is first used to open the lesion. The process can be repeated with a stent loaded onto a balloon. Direct stenting involves simultaneously performing angioplasty and stent implantation using a stent mounted on a dilatation balloon. The stent remains as a permanent scaffold after the balloon is withdrawn. A balloon capable of withstanding relatively high inflation pressures may be preferable for stent deployment because the stent must be forced against the artery's interior wall so that it will fully expand, thereby precluding the ends of the stent from hanging down into the channel, encouraging the formation of thrombus.

In adjunctive stenting, a stent delivery system with a small diameter profile is not required because the narrowing is already enlarged by the preceding device. However, in direct stenting, the stent and delivery balloon catheter need to be inserted into a stenosis that has not been previously dilated. Thus, for direct stenting to be applicable to many patients, the stent and delivery system must have a very low profile. The primary advantage of direct stenting is the procedural efficiency gained by eliminating a primary angioplasty step. The resulting procedure can be shorter and less expensive.

Primary angioplasty followed by stent placement typically requires a catheter exchange, which is usually performed over a guidewire. Given the prevalence of this staged procedure, the most commonly used balloon catheters have been over-the-wire types, having either a full length guidewire lumen or a short, distal guidewire lumen as found in rapid exchange catheters. Fixed wire, or "balloon-on-a-wire" type balloon catheters have been seldom used for primary angioplasty in stenting procedures, and these catheters have not been used to deliver stents at all. With their small size and wire-like trackability, fixed wire catheters are able to provide relatively quick and simple balloon placement and access to lesions that cannot be reached with other types of catheters. The small size of fixed wire catheters also permits their use through very small guiding catheters. However, these balloon catheters lack the ability to maintain guide wire position across a lesion and they may encounter problems re-crossing a dilated area. Thus, the present invention addresses these concerns to provide a fixed wire catheter suitable for direct stenting and accessing tortuous anatomy such as that found in the neurovascular.

SUMMARY OF THE INVENTION

The catheter of the present invention includes a wire-like metal shaft having a hollow portion defining a lumen extending therethrough. A core wire extends from a connection adjacent the distal end of the hollow portion. The connection includes multiple lateral crimps in the hollow portion, creating multiple lobes arranged around the core wire to provide communication with the lumen of the hollow portion. An elongate radiopaque tip spring is mounted to the distal tip of the core wire. A balloon is carried on the distal end of the shaft, but in a manner such that its distal end is unattached to the shaft thereby enabling the wire-like shaft to be rotated substantially independently of the balloon so that its rotation is not impaired. The proximal end of the balloon is attached to the distal end of an elongate outer tube, the proximal end of which is attached to the distal end of the hollow portion. The distal end of the balloon is attached adjacent the distal end of an inner tube, the proximal end of which is attached to and surrounds the core wire. The distal end of the inner tube extends distal to the balloon and surrounds the proximal end of the radiopaque tip spring. The balloon may be inflated and deflated through the lumen in the hollow portion, which communicates with the annular lumen defined between the outer and inner tubes.

In another embodiment of the invention, a compressed stent is mounted onto the deflated balloon of the fixed wire catheter.

An object of the invention is to provide an improved catheter and stent combination for low profile direct stenting.

Another object of the invention is to provide an improved catheter and stent combination for direct stenting in distal vascular anatomy.

Another object of the invention is to provide an improved catheter and stent combination for use through small diameter guiding catheters.

Another object of the invention is to provide an improved fixed-wire type balloon catheter.

BRIEF DESCRIPTION OF THE DRAWINGS

FIG. 1A is a cross-sectional illustration of the catheter as seen along line 1A—1A of FIG. 1;

FIG. 1B is a cross-sectional illustration of the catheter as seen along line 1B—1B of FIG. 1;

FIG. 1C is a cross-sectional illustration of the catheter as seen along line 1C—1C of FIG. 1;

FIG. 1D is a cross-sectional illustration of the catheter as seen along line 1D—1D of FIG. 1;

FIG. 1E is a cross-sectional illustration of the catheter as seen along line 1E—1E of FIG. 1;

FIG. 2 is a lateral view of the distal end of the catheter, with the balloon inflated and a stent mounted thereon.

DETAILED DESCRIPTION OF THE PREFERRED EMBODIMENTS

Figure 1:
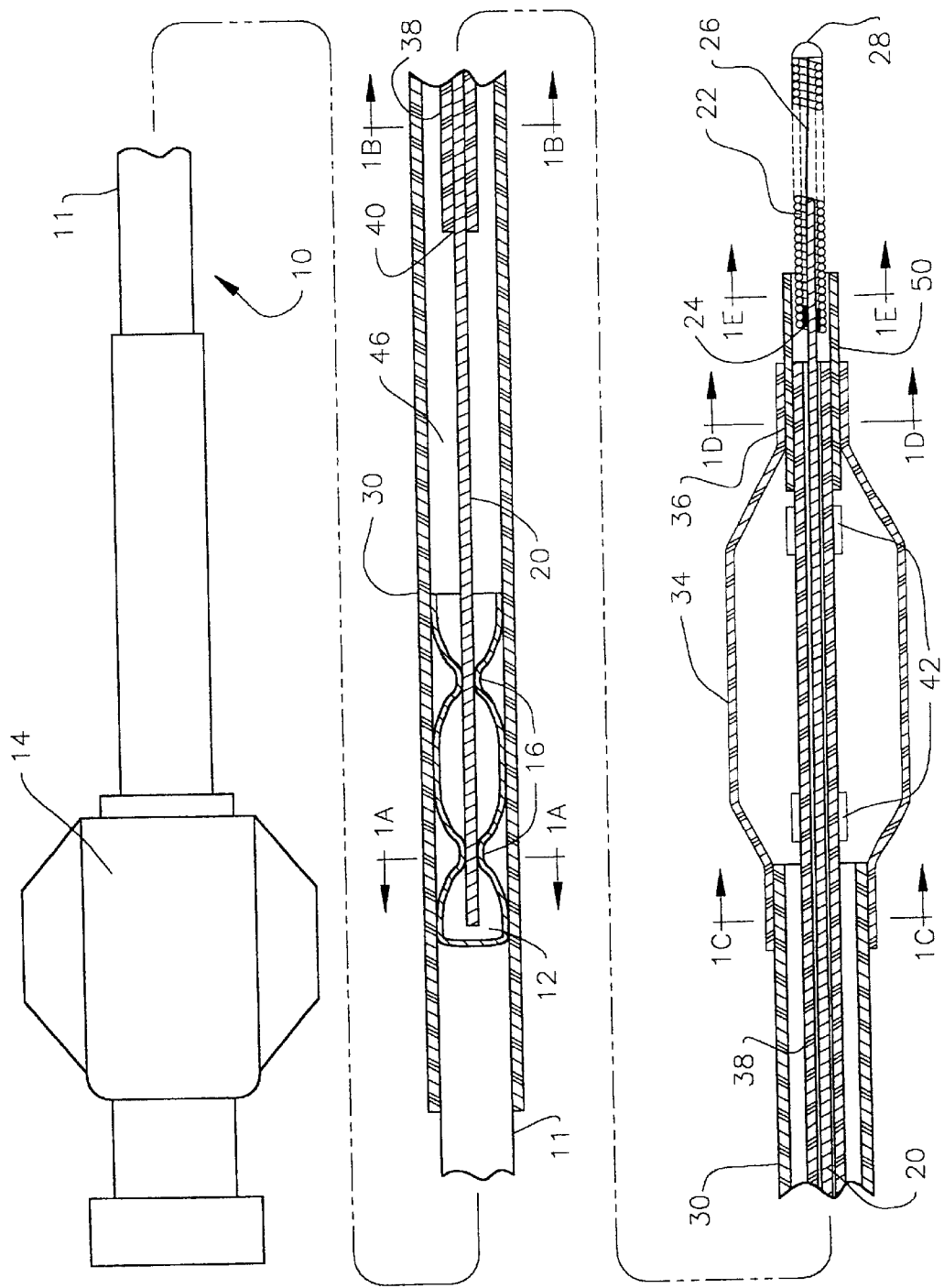
FIG. 1 is a fragmented sectional illustration of one embodiment of the catheter.

FIG. 1 shows one embodiment of the invention in which the catheter includes an elongate flexible metal shaft indicated generally by the reference character 10, and which may be preferably formed from hypotubing of stainless steel, shape memory metal or other suitable material. The overall length of the catheter may be on the order of 150 cm. The shaft 10 includes an elongate hollow proximal portion 11, about 100 cm long, and a core wire 20, about 50 cm long. By way of example, the proximal portion of the shaft may be on the order of 0.025" diameter having a wall thickness of the order of 0.0025" and may be coated with a thin film of high lubricity material, such as Teflon primer paint or the like. The proximal portion 11 defines a lumen 12, which communicates, as will be described, with the interior of the balloon 34 to inflated and deflate the balloon on the distal end of the shaft. A fitting 14 is mounted on the proximal end of the shaft 10 to facilitate connection with an inflation device, not shown, as appreciated by those of skill in the art. The shaft 10 has sufficient torsional rigidity so that it may transmit rotation effectively to the distal end of the catheter to control manipulation and steering of the distal end.

The core wire 20 is formed of stainless steel or other suitable metal wire and is attached, at its proximal end to the distal end of the proximal portion 11. To facilitate the attachment between proximal portion 11 and core wire 20, multiple lateral indentations, or crimps 16, are formed adjacent the distal end of the proximal portion. The crimps 16 are spaced around portion 11 such that the interior surfaces of the crimps 16 contact and center core wire 20 within lumen 12. The number, size and spacing of the crimps 16 provide therebetween lobes 44 in lumen 12, arranged around core wire 20. Preferably, four pairs of crimps 16 are used, as shown in FIGS. 1 and 1A, and at least one crimp is joined to core wire 20, as by welding, brazing, soldering, adhesive or the like. The core wire 20 is tapered in a distal direction so that the device is of increasing flexibility toward the distal end. By way of example, the core wire 20 may be 50 cm long and may taper from a 0.017" diameter at its proximal end to a 0.002" diameter at its distal end.

A helical tip spring 22 is secured to the distal tip of the core wire 20 as by solder joint 24 with a portion of the tip spring extending distally beyond the distal tip of the core wire 20. A stainless steel or tungsten or other material shaping ribbon 26 may be extended from solder joint 24 to a spring tip 28. The tip 28 may be soldered or the like, and is rounded to present a smooth surface. The tip spring is preferably about 25 mm long and has an outer diameter of approximately 0.012". It may be wound from 0.0025" diameter wire, such as 92% platinum and 8% tungsten alloy wire.

As shown in FIG. 1, the catheter includes an outer tube 30 that is formed from an appropriate thin flexible plastic material such as polyether block amide. The outer tube 30 is attached at its proximal end to the shaft proximal portion 11, as by heat lamination. The outer tube 30 may be of the order of 45 cm long and may have an outer diameter of about 0.037", stepping down to a diameter of about 0.030" for the distal 20 cm. The wall thickness of the outer tube 30 may be about 0.003". The distal end of the outer tube 30 is attached, as by adhesive or melt bonding, to the proximal neck of the balloon 34.

The balloon 34 may be formed by extrusion blow molding techniques that are conventional for balloons used in angioplasty or stent delivery. Some suitable materials for the balloon 34 are polyethylene terephthalate, polyether block amide, polyamide and polymer alloys or blends that may include these materials. By way of example, for use in delivering coronary stents, the body of the balloon may be from about 1 cm to 2.5 cm long, and have a diameter from about 2.0 mm to 3.5 mm. The double wall thickness of such balloons may range from approximately 0.0009" to 0.0013".

Figure 3:
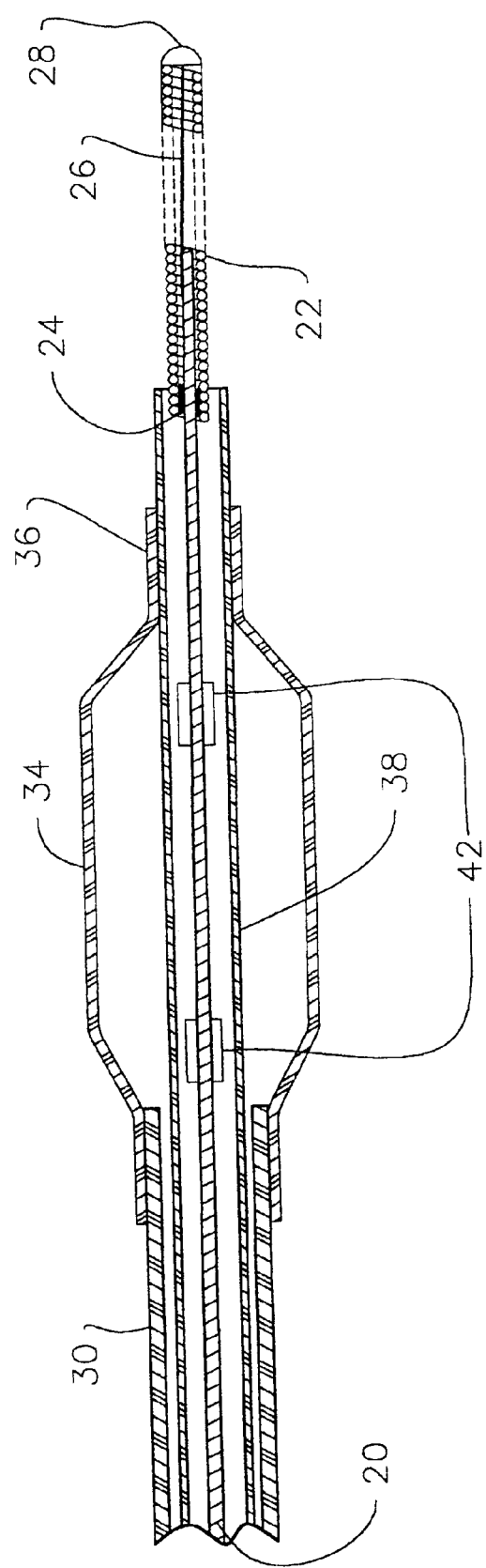
FIG. 3 is a fragmented sectional illustration of the distal portion of another embodiment of the catheter.

The distal end of the balloon 34 is attached, at its distal neck 36, adjacent the distal end of an inner tube 38 that extends proximally about the tapered core wire 20 and is attached at its proximal end to the core wire 20 by adhesive, as illustrated at 40. The inner tube 38 is thin walled and is preferably formed from thermoset polyimide. The wall thickness of the inner tube 38 is of the order of 0.001" or less. The inner tube 38 should have an inside diameter just slightly greater than the diameter of the core wire 20, and may be approximately 0.009" inside diameter. Inner tube 38 extends distally beyond balloon distal neck 36 and surrounds the proximal end of tip spring 22, as shown in FIG. 3. Preferably, inner tube 38 is extended by use of an extension tube 50 which may be bonded between balloon neck 36 and the distal end of inner tube 38, as shown in FIG. 1. Alternatively, extension tube 50 may be omitted, and the distal end of inner tube 38 may be formed with a step-up in diameter to accept the mounting of balloon neck 36, and to extend over the proximal end of tip spring 22. The inner tube 38 may be about 45 cm long. The foregoing configuration results in an inner tube 38 which displays a substantial degree of column strength to resist axial buckling of the inner tube when it is subjected to an compressive load, such as when the catheter is advanced through a patient's blood vessel. The thin wall for the inner tube 38 permits a substantial amount of rotation to be absorbed by the inner tube, yet the inner tube will not buckle under axial loads because of the support of the core wire 20.

As shown in FIG. 1, radiopaque marker bands 42 may be attached to the inner tube 38 within the balloon 34 to facilitate fluoroscopic determination of the position of the balloon in the patient's arteries. For the alternative embodiment shown in FIG. 3, radiopaque marker bands 42 may be attached to the core wire 20, within inner tube 38.

The lobes 44 communicate the inflation lumen 12 with the annular lumen 46 defined between the outer and inner tubes 30, 38. Thus, it will be appreciated that the balloon can be inflated and deflated by an inflation medium through the lumens 12 and 46, and lobes 44.

FIG. 2 illustrates a fixed-wire catheter according to the invention with a stent 55 mounted on balloon 34, which is shown in its expanded state. A distal extension of inner tube 38, or preferably, extension tube 50 may be used as follows for wrapping the balloon 34 and for loading the stent 55. The catheter may be constructed with a long extension tube 50 extending distal to the spring tip 28. Tube 50 may then be gripped by a tool distal to and without damaging tip spring 22. By pulling extension tube 50 with the tool, which is not shown, the balloon can be drawn by its distal neck 36 into a tubular fixture, not shown, to tightly wrap the balloon around the catheter shaft. A similar action may be used to draw the tightly wrapped balloon inside the stent 55, which is preferably pre-compressed to a small diameter. By pulling the balloon 34, the balloon wrapping and stent loading actions may utilize greater forces than the catheter could withstand if the balloon were being pushed instead. After the stent 55 has been loaded onto the balloon 34, extension tube 50 can be trimmed to the length shown, for example using an excimer laser, which will not damage the underlying tip spring 22.

Balloon 34 is preferably modified to retain the stent 55, using the technique disclosed in U.S. Pat. No. 5,836,965 issued to Jendersee et al. As also disclosed in Jendersee, retainers 60 may be formed on one or both ends of the balloon 34. A particular advantage of providing a proximal retainer 60 is that it will help prevent the proximal end of the stent 55 from catching on the tip of a guiding catheter, should the physician wish to remove the stent delivery catheter without deploying the stent.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. Accordingly, the present invention is not limited to the particular embodiments which have been described in detail herein.

We claim:

1. A catheter comprising:
   an elongate torque transmitting shaft having a core wire including a tip, the core wire extending distally from a radially symmetrical connection within a hollow portion, the connection having at least two lateral crimps formed in the hollow portion, the crimps touching the core wire to define open lobes arranged thereabout;
   an outer tube surrounding the core wire, a proximal end of the outer tube being coupled to the hollow portion;
   an inflatable balloon having a proximal end and a distal end, the proximal end mounted on the outer tube;
   a coiled tip spring having a proximal end coupled to the tip adjacent the distal end of the balloon;
   an inner tube surrounding the shaft beneath the outer tube and the balloon, a proximal end of the inner tube being coupled to the core wire, and a distal end of the inner tube being attached to the distal end of the balloon; and
   an inflation lumen extending from the interior of the balloon through an annular space formed between the outer and inner tubes, through the shaft connection, and through the hollow portion of the shaft.

2. The catheter of claim 1 wherein the symmetrical shaft connection has four pairs of crimps.

3. A catheter comprising:
   an elongate torque transmitting shaft having a core wire including a tip, the core wire extending distally from a radially symmetrical connection within a hollow portion, the connection having at least two lateral crimps formed in the hollow portion, the crimps touching the core wire to define open lobes arranged thereabout;
   an outer tube surrounding the core wire, a proximal end of the outer tube being coupled to the hollow portion;
   an inflatable balloon having a proximal end and a distal end, the proximal end being mounted on the outer tube;
   a tip spring having a proximal end mounted to the tip of the shaft adjacent the distal end of the balloon;
   an inner tube surrounding the shaft beneath the outer tube and the balloon, a proximal end of the inner tube being fixed to the core wire, a distal end of the inner tube being attached to the distal end of the balloon and extending distal thereto to surround the proximal end of the tip spring; and
   an inflation lumen extending from the interior of the balloon through an annular space formed between the outer and inner tubes and through the hollow portion of the shaft.

* * * * *